(12) United States Patent
Klicic Badoux et al.

(10) Patent No.: US 11,446,312 B2
(45) Date of Patent: Sep. 20, 2022

(54) COMPOUNDS THAT MODULATE VON WILLEBRAND FACTOR LEVELS AND THEIR USE IN THE TREATMENT OF BLOOD DISORDERS

(71) Applicant: SOCIETE DES PRODUITS NESTLE S.A., Vevey (CH)

(72) Inventors: Jasna Klicic Badoux, Geneva (CH); Amy Melissa Pooler, Berkeley, CA (US); Claus Rieker, Fribourg (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 16/969,426

(22) PCT Filed: Jan. 30, 2019

(86) PCT No.: PCT/EP2019/052179
§ 371 (c)(1),
(2) Date: Aug. 12, 2020

(87) PCT Pub. No.: WO2019/158359
PCT Pub. Date: Aug. 22, 2019

(65) Prior Publication Data
US 2021/0000841 A1    Jan. 7, 2021

(30) Foreign Application Priority Data
Feb. 14, 2018  (EP) ..................... 18156786

(51) Int. Cl.
| | | |
|---|---|---|
| *A61K 31/122* | (2006.01) | |
| *A61P 7/00* | (2006.01) | |
| *A61P 7/02* | (2006.01) | |
| *C07C 13/62* | (2006.01) | |
| *A61K 31/56* | (2006.01) | |

(52) U.S. Cl.
CPC ............ *A61K 31/56* (2013.01); *A61K 31/122* (2013.01)

(58) Field of Classification Search
CPC . A61K 31/122; A61P 7/00; A61P 7/02; C07C 13/62
See application file for complete search history.

(56) References Cited

U.S. PATENT DOCUMENTS

2006/0148733 A1    7/2006  Zhang et al.

FOREIGN PATENT DOCUMENTS

| | | |
|---|---|---|
| CN | 105497098 | 4/2016 |
| EP | 2070906 | 6/2009 |
| WO | 2017214709 | 12/2017 |

*Primary Examiner* — Brenda L Coleman
(74) *Attorney, Agent, or Firm* — K&L Gates LLP

(57) ABSTRACT

The present invention relates to a compound having the structure of Formula (I) for use in the prevention or treatment of a blood disorder, in particular by the modulation of von Willebrand factor levels. A nutraceutical product or food product comprising the compound of the invention 5 are also provided.

5 Claims, 1 Drawing Sheet

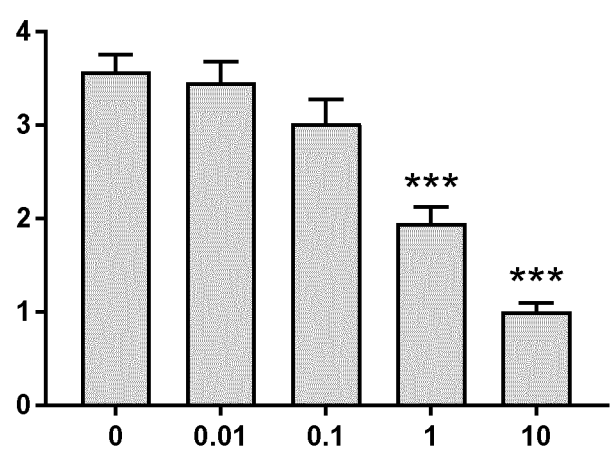

COMPOUNDS THAT MODULATE VON WILLEBRAND FACTOR LEVELS AND THEIR USE IN THE TREATMENT OF BLOOD DISORDERS

CROSS REFERENCE TO RELATED APPLICATIONS

The present application is a National Stage of International Application No. PCT/EP2019/052179, filed on Jan. 30, 2019, which claims priority to European Patent Application No. 18156786.8, filed on Feb. 14, 2018, the entire contents of which are being incorporated herein by reference.

INTRODUCTION

The cardiovascular system, comprised of the heart, blood, and blood vessels, transports nutrients, oxygen, and other elements to and from cells in the body. The walls of the blood vessels are composed of highly specialized cells called endothelial cells. These cells are involved in numerous critical functions, including barrier function, thrombosis, fibrinolysis, inflammation, angiogenesis, blood pressure, blood flow, and organ repair (Michiels, 2003).

Endothelial cells express and release von Willebrand factor (vWF), a large multimeric glycoprotein (Jaffe et al., 1973). Its principal function is to bind various proteins including factor VIII (Lollar, 1991), an essential blood-clotting protein, and blood platelet integrins (Bockenstedt et al., 1986). Therefore, vWF is crucial for platelet adhesion and thrombosis (Yau et al., 2015). Endothelial cells store vWF in secretory granules called Weibel-Palade bodies (WPBs), a dynamic storage compartment (Meyer et al., 1991). After being secreted, the large vWF multimers are cleaved by the metalloprotease ADAMTS13 (Chung & Fujikawa, 2002). Regulation of vWF exocytosis from the WPBs is tightly regulated (Rusu et al., 2014) and hypothesized to be controlled by both constituative (Giblin et al., 2008) and agonist-dependent signaling pathways (Vischer et al., 2000). Vascular injury leads to acute upregulation of vWF release and subsequent thrombosis. Overall, levels of vWF expression and release from the endothelial cells are directly linked to vWF blood levels.

Elevated blood concentrations of vWF is a predictor of cardiovascular disease (Jager et al., 1999), blood disorders (Kremer Hovinga et al., 2017), stroke (De Meyer et al., 2012), coronary heart disease (Whincup et al., 2002), rheumatoid arthritis (Gurol et al., 2015), deep-vein thrombosis (Koster et al., 1995), endothelial cell dysfunction (Horvath et al., 2004), and a number of other conditions (Franchini & Lippi, 2007). Indeed, individuals with genetic downregulation of vWF expression are protected against adverse cardiovascular events (Seaman et al., 2015). Therefore modulating of blood levels of vWF by targeting its production by endothelial cells represents an attractive point of intervention for improving disorders and diseases of the vascular system (Spiel et al., 2008). Specific compounds have been identified to modulate the activity of vWF, but none are from the class of quinone methides (Gragnano et al., 2017). This class of compounds therefore represents a novel intervention for preventing, treating, and managing blood-related disorders.

BRIEF DESCRIPTION OF THE FIGURES

FIG. 1 is a graph showing results from human endothelial cells in the experimental example disclosed herein.

DESCRIPTION OF THE INVENTION

The present invention provides a compound, particularly a terpene, particularly a triterpene, more particularly a triterpene containing quinone methide for use in the prevention or treatment of a blood disorder in a subject.

In particular, the invention relates to a compound of Formula (I) for use in the prevention or treatment of a blood disorder in a subject.

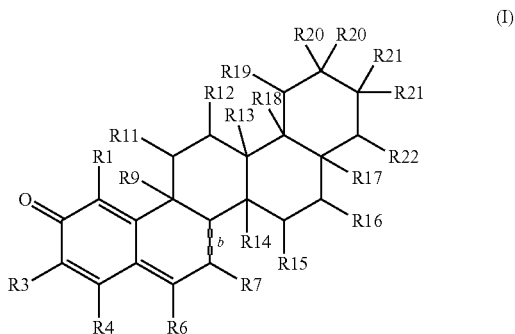

Where:

bond b is a single bond or a double bond.

R1, R4, R9, R13, R14, R17 and R20a are each independently an optionally substituted and/or optionally branched C1 to C10 alkyl, preferably a C1-5 alkyl; an optionally substituted and/or optionally branched, C2-C10 alkenyl, preferably a C2-05 alkenyl; or an optionally substituted and/or optionally branched C2 to C10 alkynyl, preferably a C2-C5 alkynyl.

More preferably, each of R1, R4, R9, R13, R14, R17 and R20a are independently a branched or unbranched saturated hydrocarbon chain having 1, 2, 3, 4, 5 or 6 carbon atoms. This term is exemplified by groups such as methyl, ethyl, n-propyl, iso-propyl, n-butyl, iso-butyl, t-butyl, n-hexyl.

More preferably at least three of R1, R4, R9, R13, R14, R17 and R20a are a methyl group. More preferably at least four of R1, R4, R9, R13, R14, R17 and R20a are a methyl group. Most preferably all of R1, R4, R9, R13, R14, R17 and R20 are a methyl group.

R3 and R20b are each independently selected from the group consisting of H, OH, —CO2H, a C1-C5 alkyl group substituted with 1 to 5 —OH, —CO2H groups.

Preferably, R3 is selected from the substituents listed in Table 1.

R6, R16 are independently H or OH

R7 is independently H, OH, or carbonyl

R12 is independently H or methyl

R11, R19 are independently H, or Br

R15 is independently H, OH, or carbonyl

R18 is independently H, methyl or OH

R21a is independently H, methyl, OH, carbonyl, or oxime.

R21b is independently nothing, H, OH or CO2H.

R22 is independently H, OH, carbonyl or an ester derivative of OH.

TABLE 1
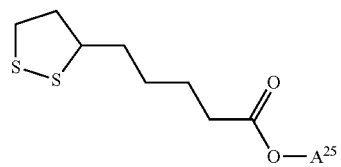
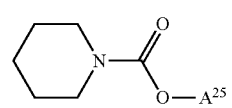
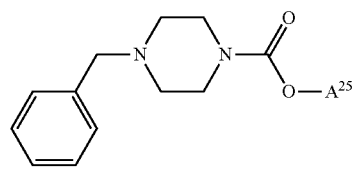
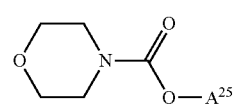
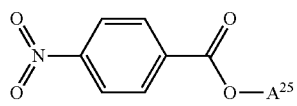
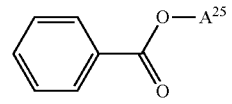
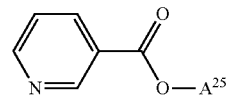
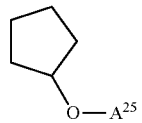
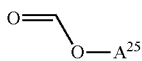
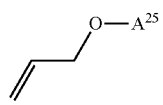
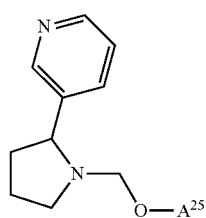
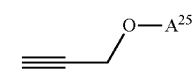
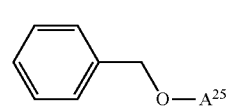
TABLE 1-continued
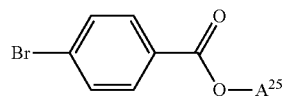
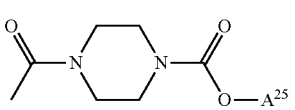
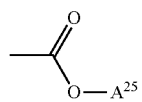
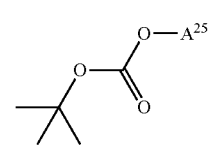
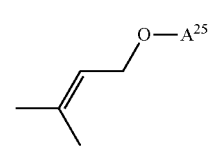
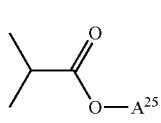
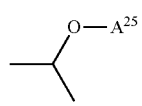
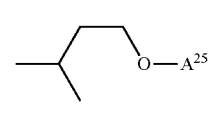
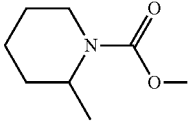
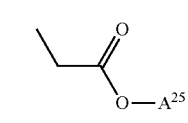
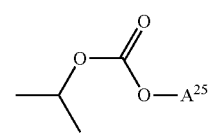
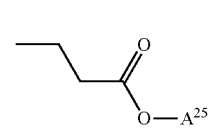

TABLE 1-continued

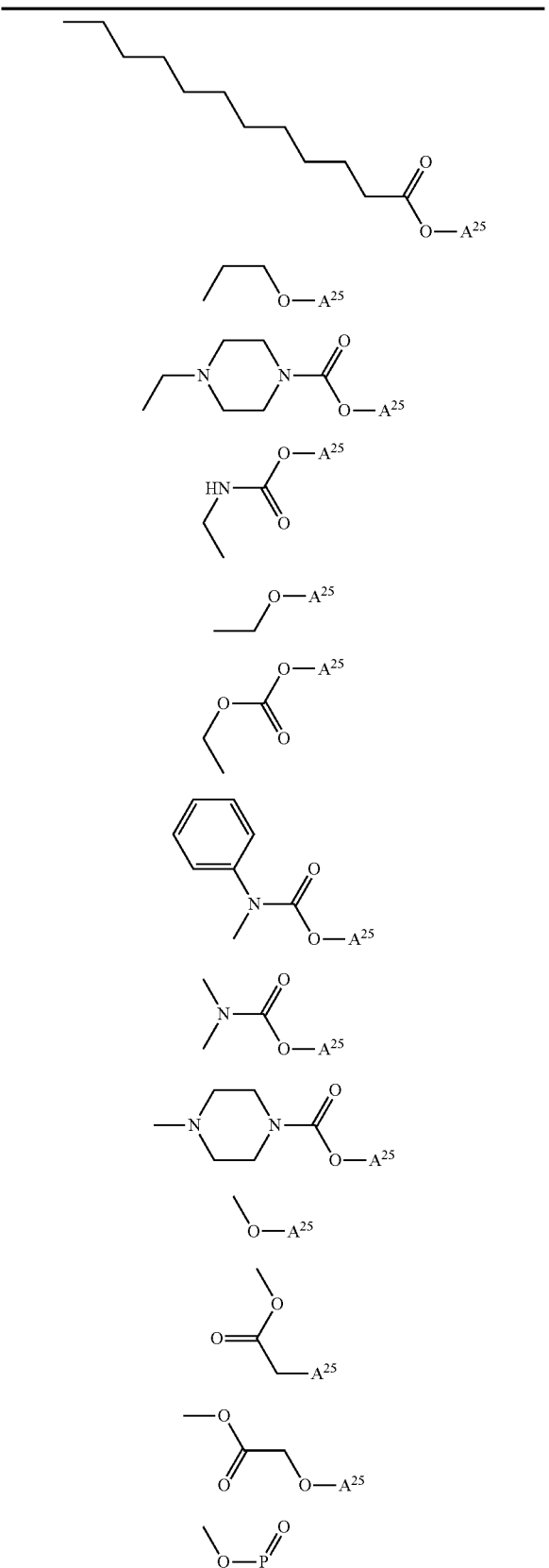

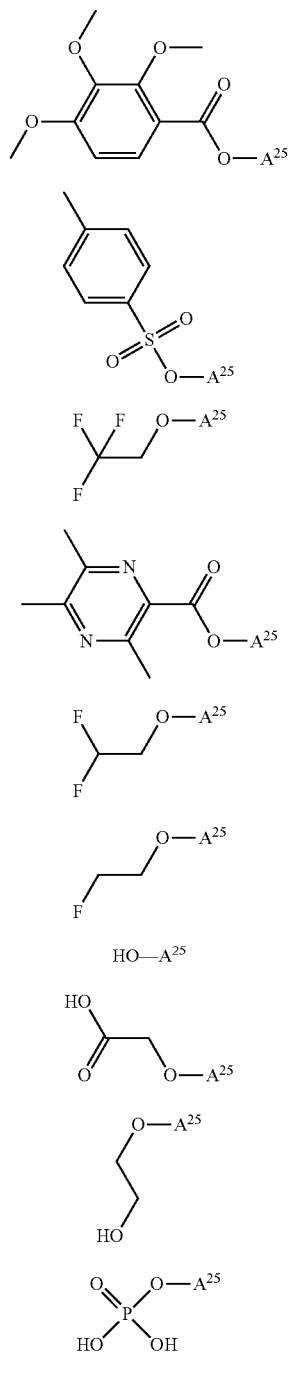

$^{25}$A—H

In a preferred embodiment, bond b is a double bond.

In a preferred embodiment, R3 is OH.

In a preferred embodiment, R20 is CO2H.

In a preferred embodiment, R3 is OH and R20 is CO2H

In a preferred embodiment, the compound of Formula (I) is a triterpene containing quinone methide.

In a preferred embodiment, the triterpene containing quinone methide compound of Formula (I) is Celastrol and has the structure of compound 1:

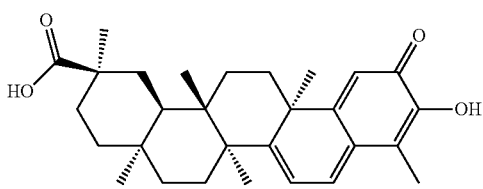

Celastrol has an empirical formula (Hill notation) C29H38O4. It has a molecular weight of 450.61. The CAS number is 34157-83-0. It has the synonym 10-Hydroxy-2,4a,6a,9,12b,14a-hexamethyl-11-oxo-1,2,3,4,4a,5,6,6a,11,12b,13,14,14a,14b-tetradecahydro-picene-2-carboxylic acid.

In one embodiment of Formula (I), R3 is OH and R20 is COOH.

In a particular embodiment, the compound of Formula (I) has the structure of compound 2:

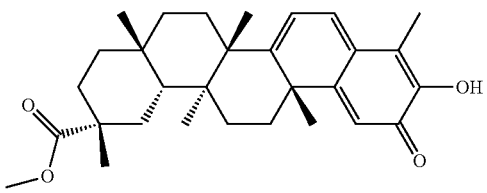

In one embodiment of Formula (I), R3, R4, R6 are independently OH; and R20 is COOH In a particular embodiment, the compound of Formula (I) has the structure of compound 3:

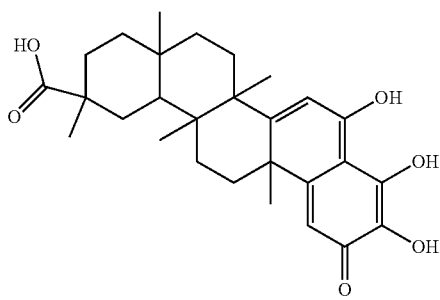

The present invention further relates to a triterpene compound of Formula (IIIa) for use in the prevention or treatment of a blood disorder in a subject:

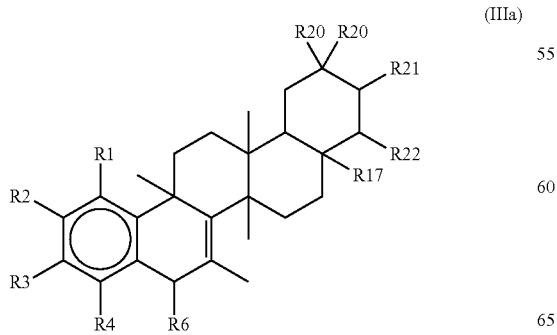

(IIIa)

Where:
Ring A is aromatic;
R2 is independently OH, methoxy, O-linked derivatives selected from ether, ester, carbonate, or glycoside. Preferably, R2 is selected from the substituents listed in Table 2a;
R3 is the same as R2 or is acetyl;
R2-R3 may form a ring;
R4 is independently H, methyl, CH2OH, OH, CO2H, CO2CH3, or formyl;
R6 is independently H, OH, carbonyl, acetyl, nitrile, allyl, or alkyl groups containing OH, amino, keto or ester groups, S-linked group, heteroaryl, or as defined in table 2b;
R7 is independently H, or OH;
R17 is independently H, or methyl;
R20a is independently methyl, CH2OH or acetyl-ester derivative or as defined in table 2c; and
R20b is independently H, OH, CH2OH, or acyl derivatives including carboxylic acids, amides, esters; or nitrile, N-linked groups including amines, amides, urea and its derivatives, or as defined in table 2d;
R21 is independently H, OH, carbonyl, or O-linked acetate ester; and
R22 is independently H, methyl, OH, or O-linked acetate ester TABLE 2a

| (examples of substituent R2): |
|---|
| 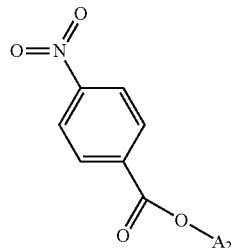 |
| 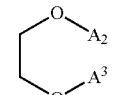 |
| 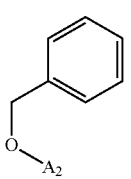 |
| 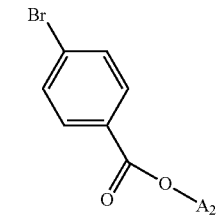 |
| 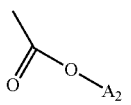 |

TABLE 2a-continued
(examples of substituent R2):
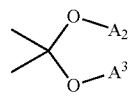
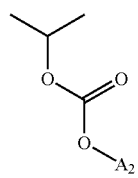
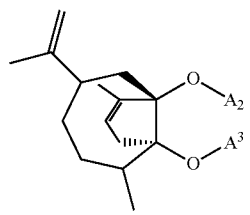
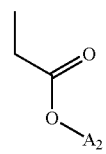
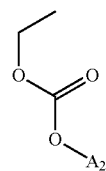
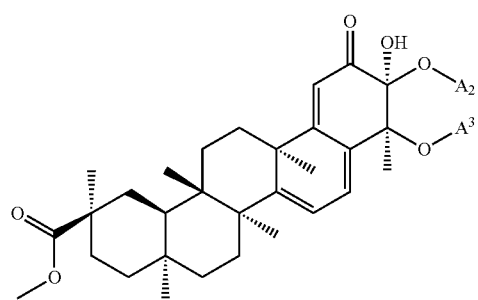
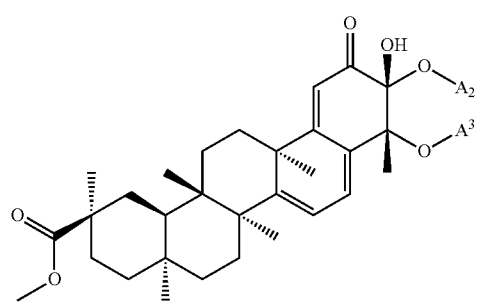
TABLE 2a-continued
(examples of substituent R2):
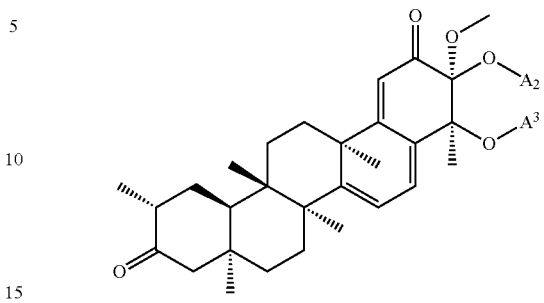
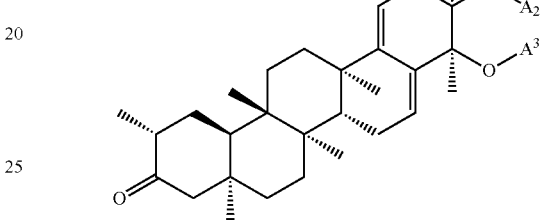
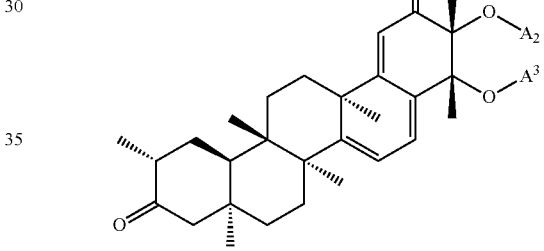
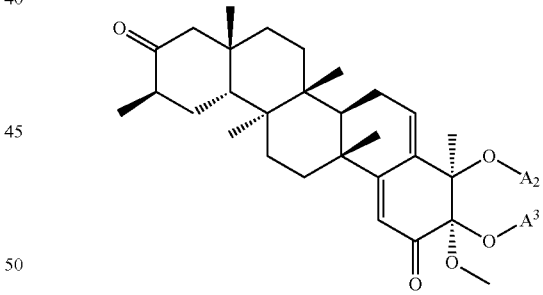
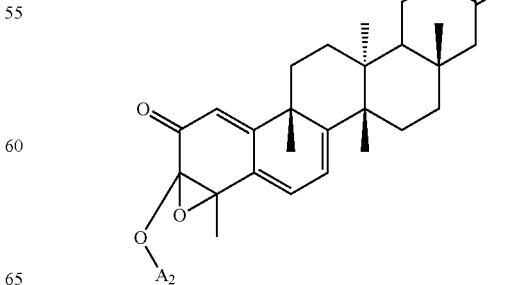

TABLE 2a-continued
(examples of substituent R2):
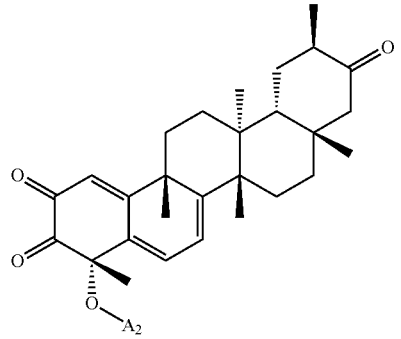
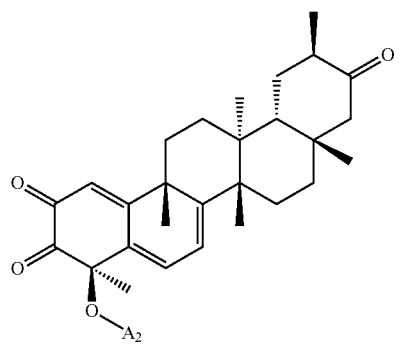
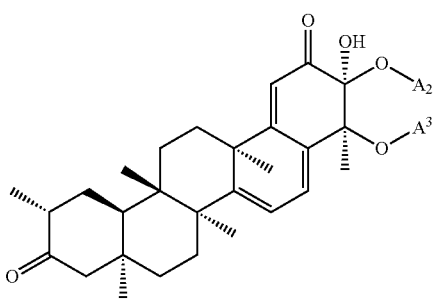
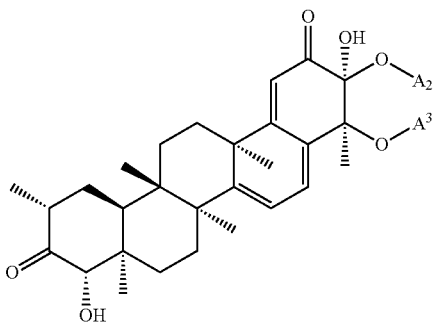
TABLE 2a-continued
(examples of substituent R2):
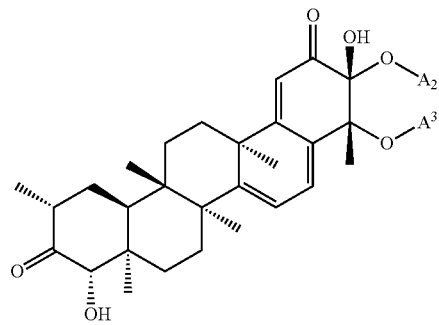
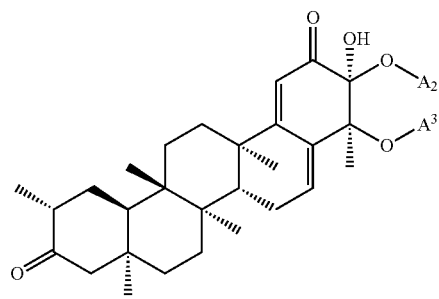
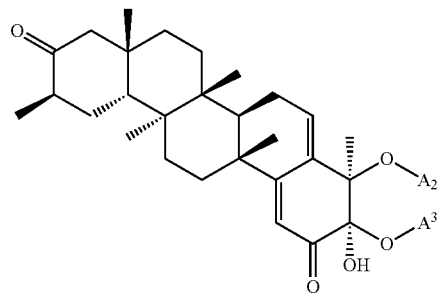
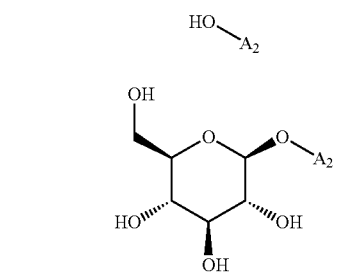
TABLE 2b
(examples of substituent R6):
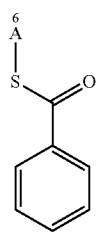

TABLE 2b-continued
(examples of substituent R6):
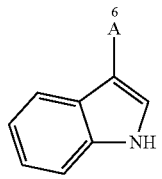
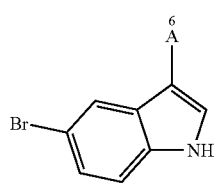
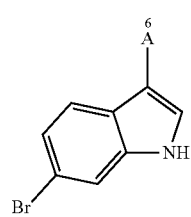
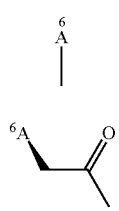
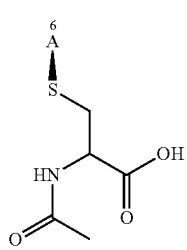
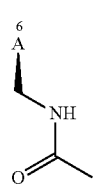
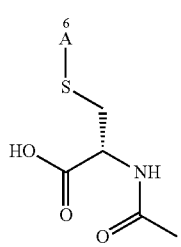
TABLE 2b-continued
(examples of substituent R6):
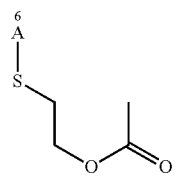
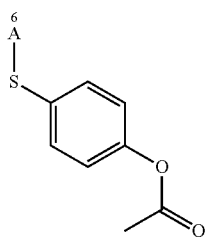
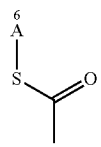
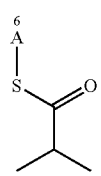
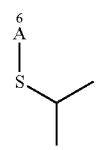
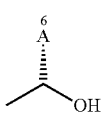
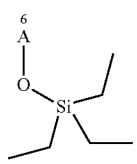
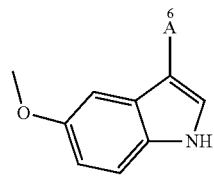

TABLE 2b-continued
(examples of substituent R6):
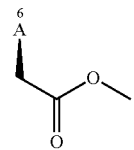
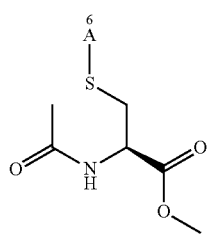
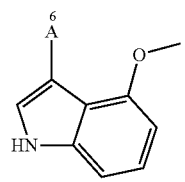
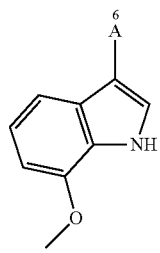
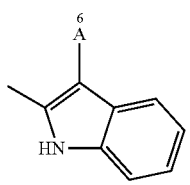
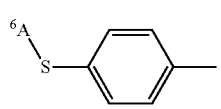
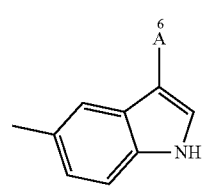
TABLE 2b-continued
(examples of substituent R6):
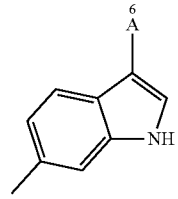
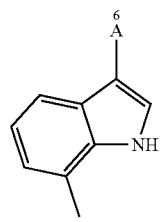
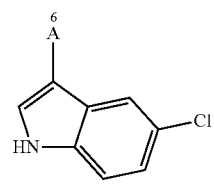
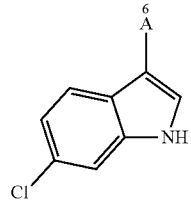
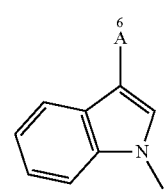
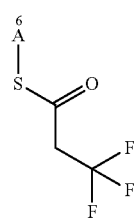
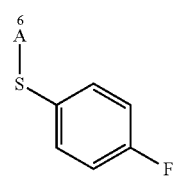

TABLE 2b-continued
(examples of substituent R6):
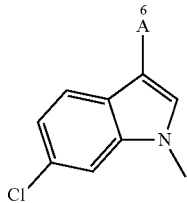
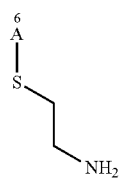
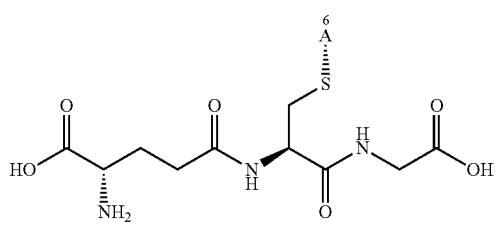
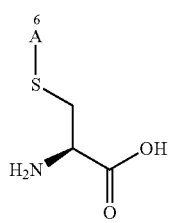
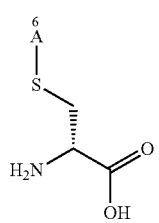
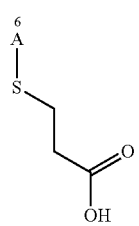
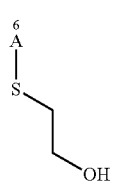
TABLE 2b-continued
(examples of substituent R6):
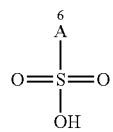
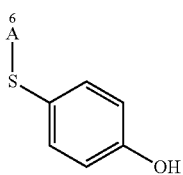
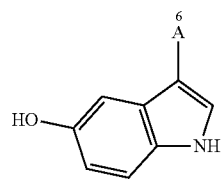
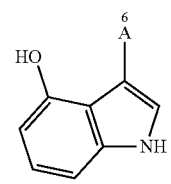
A6; (v1)
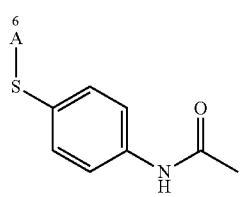
TABLE 2c
(examples of substituent R20a):
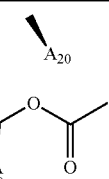
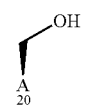

TABLE 2d (examples of substituent R20b):

TABLE 2d-continued (examples of substituent R20b):

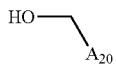

A20; (v1)

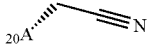

In one embodiment, the compound of Formula (IIIa) has the structure of compound 6:

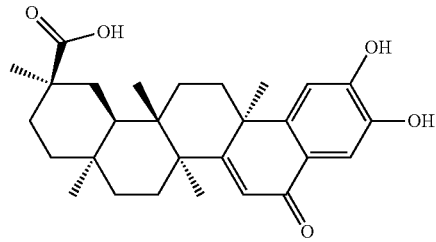

In one embodiment, the compound of Formula (IIIa) has the structure of compound 7:

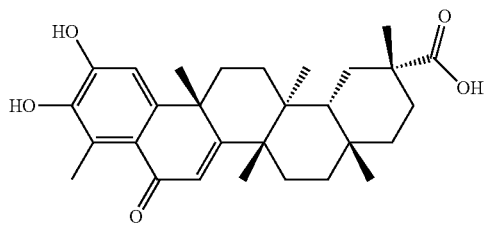

In one preferred embodiment, R2 is OH.
In one preferred embodiment, R3 is OH.
In one preferred embodiment, R4 is CO.
In one preferred embodiment, R6 is CO.
In one preferred embodiment, R20 is COOH.
In one preferred embodiment R2 and R3 are OH, R4 and R6 are CO, and R20 is COOH.

In one particular preferred embodiment, the compound of Formula (IIIa) is not a quinone methide compound.

In one particular preferred embodiment, the compound of Formula (IIIa) has the structure of compound 8:

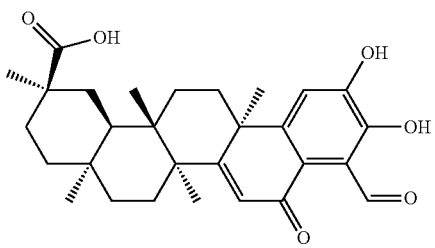

Compound 8 has an empirical formula (Hill notation) C29H36O6. It has a molecular weight of 480.601.

In one embodiment, the compound of Formula (111a) has the structure of compound 9:

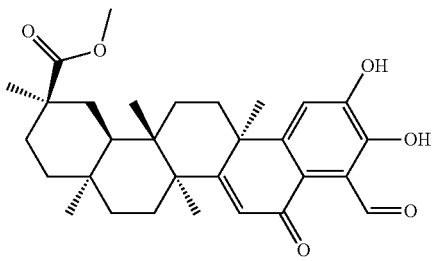

In one preferred embodiment, R2 is OH.
In one preferred embodiment, R3 is OH.
In one preferred embodiment, R6 is COH.
In one preferred embodiment, R20 is COOH.
In one preferred embodiment R2 and R3 are OH, R6 is COH and R20 is COOH.

In one particular preferred embodiment, the compound of Formula (IIIa) is not a quinone methide compound.

In one embodiment, the compound of Formula (IIIa) has the structure of compound 10:

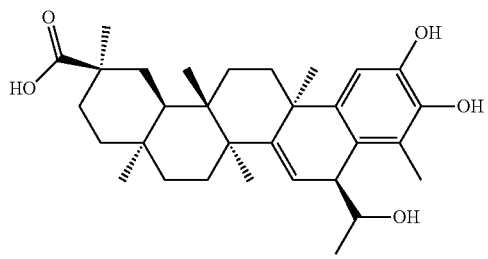

Compound 10 has an empirical formula (Hill notation) C31H44O5. It has a molecular weight of 496.688. It is not a quinone methide compound.

In one embodiment, the compound of Formula (IIIa) has the structure of compound 11:

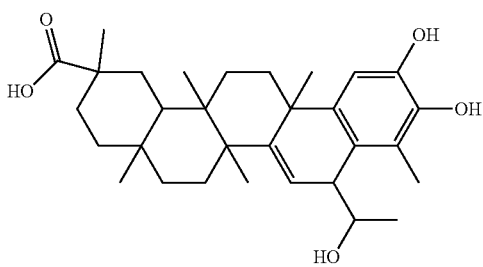

The present invention further relates to a triterpene compound of Formula (IIIb) for use in the prevention or treatment of a blood disorder in a subject:

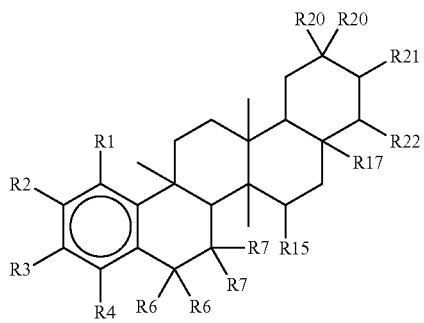

Where

R2, R3 is independently OH, methoxy, or O-linked acetyl ester;

R4 is independently is independently H, methyl, CHO, or CO2H;

R6a is independently: H, or carbonyl and R6b is independently H, or sulfonate;

R7a is independently H, or carbonyl and R7b is independently H, or OH;

R15 is independently H, or OH;

R17 is independently H, or methyl;

R20a is independently methyl, OH, or CO2H and R20b is independently H, carbonyl, CO2H, or CO2CH3;

R21 is independently H, or carbonyl; and

R22 is independently H, OH, or O-linked acetyl ester.

The present invention further relates to a triterpene compound of Formula (IVa) for use in the prevention or treatment of a blood disorder in a subject:

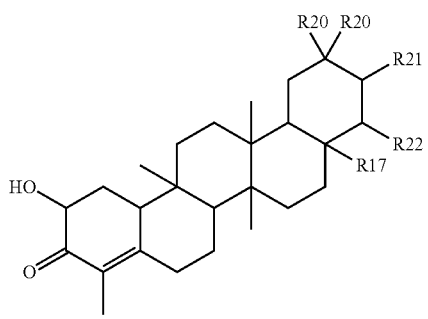

(IVa)

Where

R6 and R22 are independently H, or OH;

R20a is methyl and R20b is independently H, or CO2H;

R21 is independently H, or carbonyl.

In one embodiment, the compound of Formula (IVa) has the structure of compound 12:

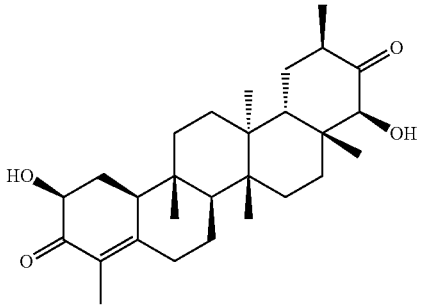

In one embodiment, the present invention provides a triterpene compound of Formula (IVb) for use in the prevention or treatment of a blood disorder in a subject:

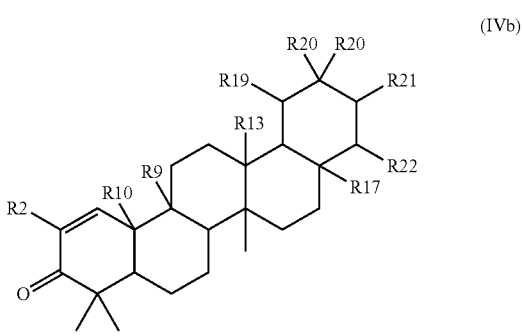

(IVb)

Where

R2 is independently OH, or O-linked acetyl ester

R9, R10, R13, R19 are independently H, or methyl

R17 is methyl

R17, R19 may also form an intramolecular ring containing an ether or ester group R20a is methyl and R20b is independently methyl or forms an ester-containing intramolecular ring to position 17

In one embodiment, the present invention provides a triterpene compound of Formula (IVc) for use in the prevention or treatment of a blood disorder in a subject:

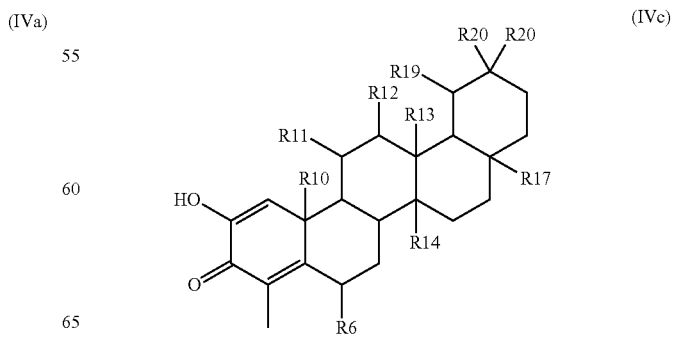

(IVc)

Where
R6 is independently H, or OH
R8, R10, R14 are methyl
R11, R12 are epoxide
R13-R17 are an ester containing ring
R19 is independently H, or methyl
R20a is independently methyl, or methylene and R20b is independently H, methyl, or OH In one embodiment, the present invention provides a triterpene compound of Formula (V) for use in the prevention or treatment of a blood disorder in a subject:

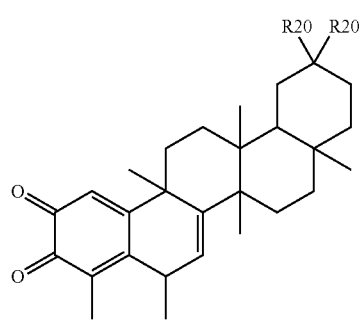

(V)

Where
R20a is methyl and R20b is independently CO2H or ester and amide derivatives.

The present invention provides a compound, particularly a diterpene, more particularly a diterpene containing quinone methide compound of Formula (II) for use in the prevention or treatment of a blood disorder in a subject:

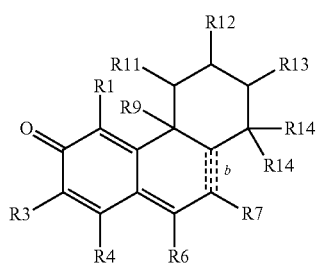

(II)

Where:
bond b is a single or a double bond
R1 is independently H, OH, or O-linked acetate ester (OAc)
R3 may be selected from the substituents listed in Table 3
R4 is independently H, methyl, isopropyl, OH, methoxy, OAc, or CH2CH2OH
R3, R4 can also form an ether-containing ring
R6 is independently H, OH, methoxy, NH2, or (CH2)4C(=O)CH3, diterpene
R7 is independently H, OH, OMe, carbonyl, or Br
R7, R14 can also form an ether containing ring
R9 is independently methyl, CO2Me, or CH2CO2Me
R12 is independently H, OH, carbonyl, O-linked acetate ester or O-linked benzoate ester (derivatives)
R13 is independently H, OH, carbonyl, O-linked formate ester, O-linked benzoate ester, or O-linked cinnamate ester R14a is independently methyl, CH2OH, or CH2O-linked ester and R14b is methyl
R3 can be further defined as follows:

TABLE 3

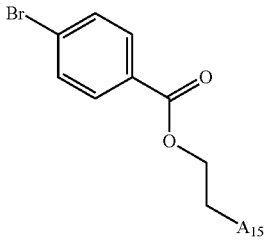

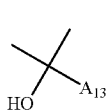

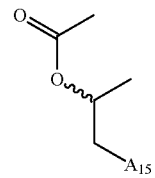

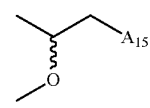

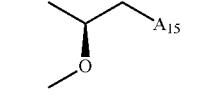

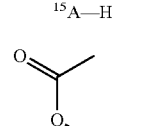

TABLE 3-continued

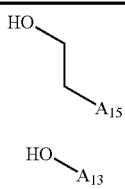

In one embodiment, the compound of Formula (II) has the structure of compound 4:

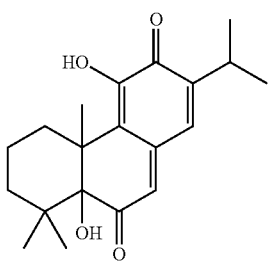

In one preferred embodiment, R6 is O
In one preferred embodiment, R11 is OH
In one preferred embodiment, R12 is O
In one preferred embodiment R6 and R12 are O, and R11 is OH
In one particular preferred embodiment, the compound of Formula (111a) is a quinone methide compound.
In one particular preferred embodiment, the compound of Formula (II) is a diterpene quinone methide and has the structure of compound 5:

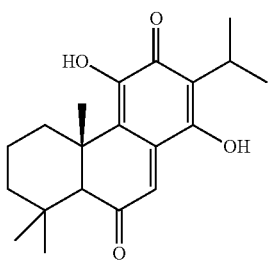

Compound 5 has an empirical formula (Hill notation) C20H26O4. It has a molecular weight of 330.424.

In one embodiment, the present invention provides a diterpene compound of Formula (VIIa) for use in the prevention or treatment of a blood disorder in a subject:

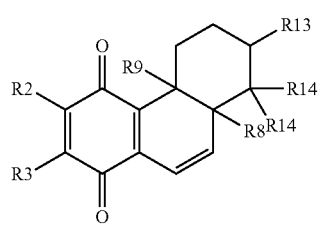

(VIIa)

Where:
R2 is independently OH, methoxy, allyloxy, or O-linked acetyl ester
R3 is independently H, n-propyl, isopropyl, allyl, or isopropyl derivative with acetyl ester group
R8 is independently H, or OH
R9 is methyl
R13 is independently H, OH, or O-linked formate ester
R14 is independently methyl, or CH2OH and its formate ester
R9, R14 can be an ester-containing ring In one embodiment, the compound of Formula (VIIa) has the structure of compound 13:

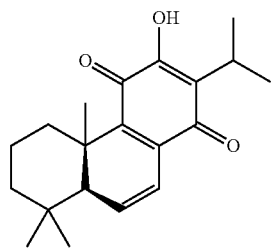

In one embodiment, the present invention provides a diterpene compound of Formula (VIIb) for use in the prevention or treatment of a blood disorder in a subject:

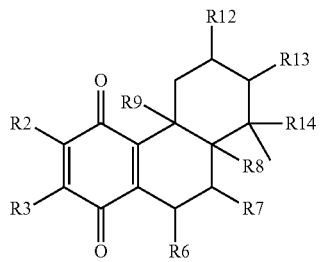

(VIIb)

Where:
R2 is independently OH, methoxy, an ether derivative or an ester derivative
R3 is independently H, isopropyl, allyl, isopropenyl, or n-propyl and isopropyl derivatives containing hydroxyl, ether and ester groups
R6 is independently H, methyl, OH, methoxy, ethoxy, carbonyl, O-linked formate, acetate, hydroxyacetate or fatty acid ester
R7 is independently H, OH, carbonyl, O-linked formate, acetate, propionate, butyrate or benzoate ester and derivatives thereof
R8 is independently H, or methoxy R9 is independently methyl, CH2OH, or carboxylic acid
R9, R14 is independently hydroxyl, ether or ester group containing ring
R12 is independently H, or OH
R13 is independently H, OH, carbonyl, or an O-linked formate or acetate ester
R14 is independently methyl, CH2OH or its formate or acetate esters, or CO2CH3

In one embodiment, the compound of Formula (VIIb) has the structure of compound 14:

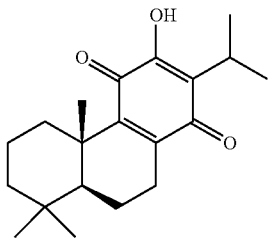

In one embodiment, the compound of Formula (VIIb) has the structure of compound 15:

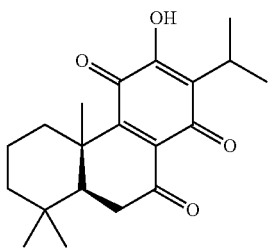

In one preferred embodiment, R12 is OH.

In one particular preferred embodiment, the compound of Formula (VIIb) is not a quinone methide compound.

In one particular preferred embodiment, the compound of Formula (VIIb) is a diterpene and has the structure of compound 16:

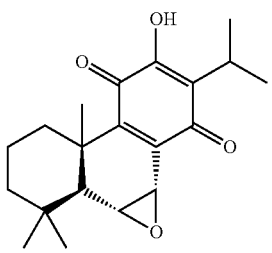

Compound 16 has an empirical formula (Hill notation) C20H26O4. It has a molecular weight of 330.424. It is not a quinone methide compound.

In one embodiment, the compound of Formula (VIIb) has the structure of compound 17:

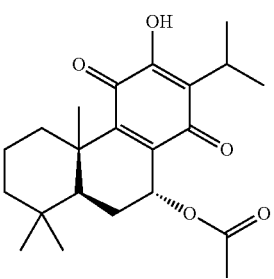

In one embodiment, the compound of Formula (VIIb) has the structure of compound 18:

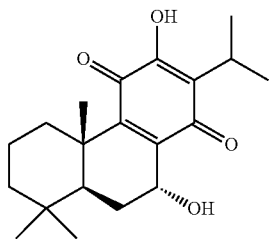

In one embodiment, the compound of Formula (VIIIb) has the structure of compound 19:

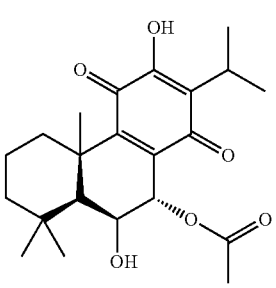

In one embodiment, the compound of Formula (VIIIb) has the structure of compound 20:

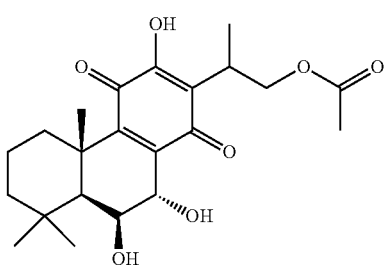

In one embodiment, the compound of Formula (VIIIb) has the structure of compound 21:

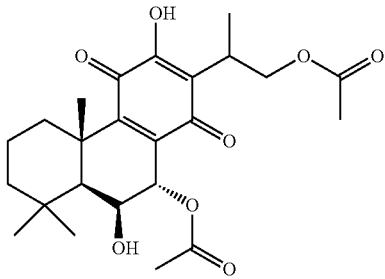

In one embodiment, the compound of Formula (VIIb) has the structure of compound 22:

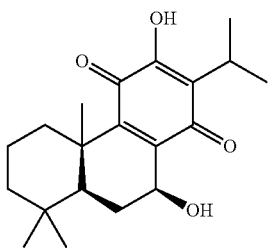

In one embodiment, the compound of Formula (VIIb) has the structure of compound 23:

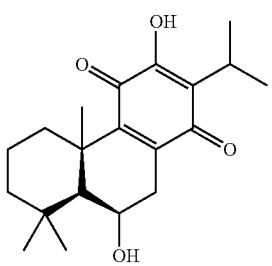

In one embodiment, the compound of Formula (VIIb) has the structure of compound 24:

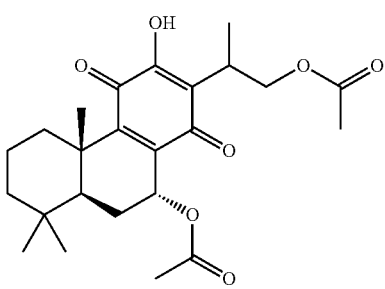

In one embodiment, the compound of Formula (VIIb) has the structure of compound 25:

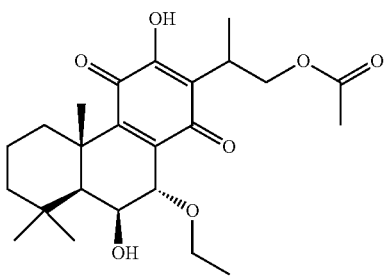

In one embodiment, the present invention provides a diterpene compound of Formula (VIIIa) for use in the prevention or treatment of a blood disorder in a subject:

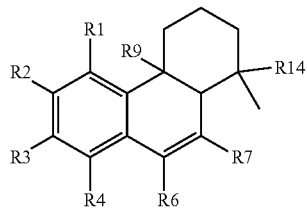

(VIIIa)

Where:
R1, R2, R4 are independently OH, methoxy, or an O-linked acetate ester
R3 is independently H, isopropyl, propen-1-yl, propen-2-yl, or acetyl ester derivatized n-propyl
R6 is independently H, or acetyl
R7 is H
R7, R14 can be ether containing rings
R9 is independently methyl, or CO2H
R14 is methyl In one embodiment, the present invention provides a diterpene compound of Formula (VIIIb) for use in the prevention or treatment of a blood disorder in a subject:

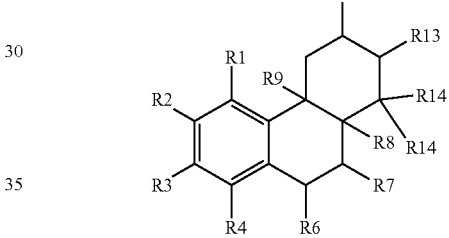

(VIIIb)

Where:
R1 is independently OH, methoxy, or O-linked acetate ester
R2 is independently OH, methoxy, O-linked acetate or benzoate ester
R3 is independently: H, linear and branch alkyl or alkenyl and derivatives containing OH, ether or ester group
R2, R3 can be ether containing rings
R4 is independently OH, methoxy, or O-linked acetate ester
R3, R4 can be ether containing rings
R6 is independently H, OH, methoxy, carbonyl, or 0-linked acetate ester
R6, R7, R8, R9, and R14 can be independently ester containing rings
R7 is independently H, OH, methoxy, carbonyl, O-linked acetate ester
R8 is independently H, methyl, CH2OH, or formyl
R9, R14 can be ether or ester containing rings
R12 is independently H, OH, or O-linked acetate ester
R13 is independently H, OH, carbonyl, methylene, or O-linked formate or acetate ester
R14 is independently methyl, methylene, CH2OH formate ester, or CO2CH3
In one preferred embodiment, R1 is OH
In one preferred embodiment, R2 is OH
In one preferred embodiment, R4 is OH
In one preferred embodiment, R6 is CO
In one preferred embodiment, R7 is CO In one preferred embodiment, R1, R2 and R4 are OH; and R6 and R7 are CO In one particular preferred embodiment, the compound of Formula (VIIb) is not a quinone methide compound.

In one particular preferred embodiment, the compound of Formula (VIIIb) has the structure of compound 26:

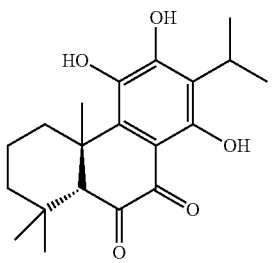

Compound 26 has an empirical formula (Hill notation) C20H26O5. It has a molecular weight of 346.423. It is not a quinone methide compound.

In one embodiment, the compound of Formula (VIIIb) has the structure of compound 27:

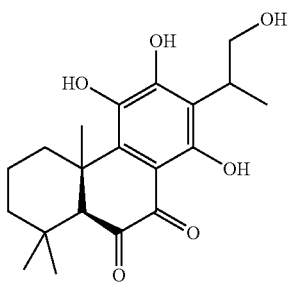

In one embodiment, the compound of Formula (VIIIb) has the structure of compound 28:

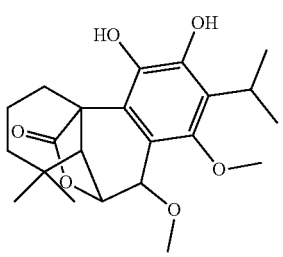

In one embodiment, the compound of Formula (VIIIb) has the structure of compound 29:

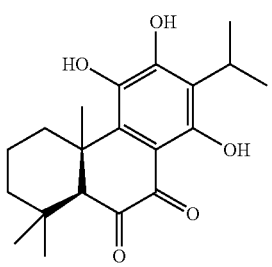

In one embodiment, the present invention provides a diterpene compound of Formula (IX) for use in the prevention or treatment of a blood disorder in a subject:

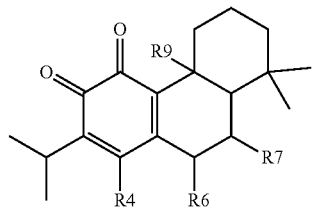

Where:
R4 is independently OH, or methoxy
R6 is independently OH, or O-linked acetyl ester
R7 is H
R9 is methyl
R7, R9 can be ester containing rings In one embodiment, the present invention provides a diterpene compound of Formula (X) for use in the prevention or treatment of a blood disorder in a subject:

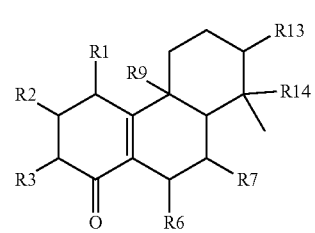

Where:
R1 is independently H, OH, carbonyl, or O-linked acetyl ester
R2 is independently OH, epoxide, or O-linked acetyl ester
R3 is independently H, methyl, epoxide, isopropyl, or 1,2-propylene and its ester derivatives
R6 is independently H, OH, ethoxy, carbonyl, O-linked formate, acetate or benzoate ester derivatives
R7 is independently H, OH, or O-linked acetyl ester
R9 is methyl
R13 is independently H, OH, carbonyl, 1,4-butylene derivative, O-linked formate or acetate ester
R6, R9 can be a double bond containing ring
R14 is independently methyl, 1,4-butylene derivative, CH2OH or its formate or acetate ester, or CO2CH3

In one embodiment, there is provided a compound according to the invention for use in the prevention or treatment of a blood disorder by modulation of von Willebrand factor levels in a subject.

In one embodiment, there is provided a compound according to the invention for use in the prevention of a blood disorder by modulation of von Willebrand factor levels in a subject.

In one embodiment, there is provided a compound according to the invention for use in the treatment of a blood disorder by modulation of von Willebrand factor levels in a subject.

In one embodiment, there is provided a compound according to the invention for use in the prevention or treatment of a blood disorder by lowering of von Willebrand factor levels in a subject.

In one embodiment, there is provided a compound for use according to the invention wherein said compound is a triterpene compound selected from compounds 1, 2, 3, 6, 7, 8, 9, 10, 11 and 12 as described herein.

In one embodiment, there is provided a compound for use according to the invention wherein said compound is a triterpene quinone methide selected from celastrol (compound 1), friedelin, pristimerin, and tingenone.

In one embodiment, there is provided a compound for use according to the invention wherein said compound is celastrol (compound 1).

In one embodiment, there is provided a compound for use according to the invention wherein said compound is a triterpene non quinone methide compound.

In one embodiment, there is provided a compound for use according to the invention wherein said triterpene non quinone methide compound is selected from compounds 8 and 10. Compound 8 can be described as having formula $C_{31}H_{44}O_5$ and molecular weight of 480.601. Compound 10 can be described as having formula $C_{31}H_{44}O_5$ and molecular weight of 496.688.

In one embodiment, there is provided a compound for use according to the invention wherein said compound is a diterpene selected from compounds 4, 5, 13, 14, 15, 16, 17, 18, 19, 20, 21, 22, 23, 24, 25, 26, 27, 28, and 29 as described herein.

In one embodiment, there is provided a compound for use according to the invention wherein said compound is diterpene quinone methide compound 5. Compound 5 can be described as having formula $C_{20}H_{26}O_4$ and molecular weight of 330.424.

In one embodiment, there is provided a compound for use according to the invention wherein said compound is a diterpene non quinone methide compound.

In one embodiment, there is provided a compound for use according to the invention wherein said compound is a diterpene non quinone methide selected from compounds 16 and 26. Compound 16 can be described as having formula $C_{20}H_{26}O_4$ and molecular weight of 330.424. Compound 26 can be described as having formula $C_{20}H_{26}O_5$ and molecular weight of 346.423.

In one embodiment, there is provided a compound for use according to the invention wherein the blood disorder is one or more of von Willebrand Factor disease, thrombosis, hemostasis, hypercoagulation, abnormal blood flow, and endothelial cell dysfunction.

In one embodiment, there is provided a compound for use according to the invention wherein the blood disorder is thrombosis, particularly a peripheral, cardiac, or cerebral thrombosis.

In one embodiment, there is provided a compound for use according to the invention wherein the blood disorder is hemostasis.

In one embodiment, there is provided a compound for use according to the invention wherein said subject has a condition associated with higher levels of von Willebrand factor.

In one embodiment, there is provided a compound for use according to the invention wherein said higher levels of von Willebrand factor are due to one or more of: the presence of the ApoE4 allele, cardiovascular disorders, Type I diabetes, Type 2 diabetes, Systemic lupus erythematosus, Active ulcerative colitis, Rheumatoid arthritis, physiological and acute stress, including surgery, exercise, anxiety, systemic inflammation, pregnancy.

In one embodiment, there is provided a compound for use according to the invention wherein said higher levels of von Willebrand factor are due to the presence of the ApoE4 allele in a subject. ApoE4 is a well-known genetic risk factor for cardivascular disorders. In one embodiment, said subject has an ApoE4/ApoE4 genotype. In one embodiment, said subject has an ApoE3/ApoE4 genotype. In one embodiment, said subject has an ApoE3/ApoE3 genotype.

In one embodiment, the compound or composition thereof is administered by oral administration. In one embodiment, the compound or composition thereof is administered by intravenous administration.

In one embodiment, the subject is a human being, for example an elderly human being.

There is also provided a nutraceutical product or food product comprising a triterpene or diterpene compound, particularly a triterpene quinone methide or diterpene quinone methide.

In one embodiment, the compound is selected from Celastrol (10-Hydroxy-2,4a,6a,9,12b,14a-hexamethyl-11-oxo-1,2,3,4,4a,5,6,6a,11,12b,13,14,14a,14b-tetradecahydro-picene-2-carboxylic acid), friedelin, primisterin, and tingenone.

In one embodiment, the compound is Celastrol (10-Hydroxy-2,4a,6a,9,12b,14a-hexamethyl-11-oxo-1,2,3,4,4a,5,6,6a,11,12b,13,14,14a,14b-tetradecahydro-picene-2-carboxylic acid).

There is also provided the use of a nutraceutical product or food product according to the invention for the prevention or treatment of a blood disorder in a subject.

In one embodiment, the blood disorder is thrombosis. In another embodiment, the blood disorder is hemostasis.

In one embodiment, the subject has an ApoE3/ApoE4 genotype. In another embodiment, the subject has an ApoE4/ApoE4 genotype.

Definitions

All percentages expressed herein are by weight of the total weight of the composition unless expressed otherwise. As used herein, "about," "approximately" and "substantially" are understood to refer to numbers in a range of numerals, for example the range of –10% to +10% of the referenced number, preferably -5% to +5% of the referenced number, more preferably –1% to +1% of the referenced number, most preferably –0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The term "alkyl" refers to a monoradical branched or unbranched saturated hydrocarbon chain having from 1 to 20 carbon atoms, or from 1 to 15 carbon atoms, or from 1 to 10 carbon atoms, or from 1 to 8 carbon atoms, or from 1 to 6 carbon atoms, or from 1 to 4 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having 1, 2, 3, 4 or 5 substituents, (in some embodiments, 1, 2 or 3 substituents) selected from the group consisting of alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —S(O)-alkyl, —S(O)-cycloalkyl, —S(O)-heterocyclyl, —S(O)-aryl, —S(O)-heteroaryl, —S(O)2 -alkyl, —S(O)2 -cycloalkyl, —S(O)2 -heterocyclyl, —S(O)2 -aryl and —S(O)2-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF3 , amino, substituted amino, cyano, cycloalkyl, heterocyclyl, aryl, heteroaryl, and —S(O)n R<a>, in which R<a> is alkyl, aryl or heteroaryl and n is 0, 1 or 2; or 2) an alkyl group as defined above that is interrupted by 1-10 atoms (e.g. 1, 2, 3, 4 or 5 atoms) independently chosen from oxygen, sulfur and NR<a>, where R<a> is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, CF3 , amino, substituted amino, cyano, cycloalkyl, heterocyclyl, aryl, heteroaryl, and —S(O)n R<a>, in which R<a> is alkyl, aryl or heteroaryl and n is 0, 1 or 2; or 3) an alkyl group as defined above that has both 1, 2, 3, 4 or 5 substituents as defined above and is also interrupted by 1-10 atoms (e.g. 1, 2, 3, 4 or 5 atoms) as defined above.

The term "heterocyclyl," "heterocycle," or "heterocyclic" refers to a monoradical saturated group having a single ring or multiple condensed rings, having from 1 to 40 carbon atoms and from 1 to 10 hetero atoms, and from 1 to 4 heteroatoms, selected from nitrogen, sulfur, phosphorus, and/or oxygen within the ring. In some embodiments, the heterocyclyl," "heterocycle," or "heterocyclic" group is linked to the remainder of the molecule through one of the heteroatoms within the ring.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The words "comprise," "comprises" and "comprising" are to be interpreted inclusively rather than exclusively. Likewise, the terms "include," "including" and "or" should all be construed to be inclusive, unless such a construction is clearly prohibited from the context. Nevertheless, the compositions disclosed herein may lack any element that is not specifically disclosed herein. Thus, a disclosure of an embodiment using the term "comprising" includes a disclosure of embodiments "consisting essentially of" and "consisting of" the components identified. A composition "consisting essentially of" contains at least 50 wt. % of the referenced components, preferably at least 75 wt. % of the referenced components, more preferably at least 85 wt. % of the referenced components, most preferably at least 95 wt. % of the referenced components.

The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive.

"Prevention" includes reduction of risk and/or severity of a condition or disorder. The terms "treatment," "treat," "attenuate" and "alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder, and include treatment of patients at risk of contracting a disease or suspected to have contracted a disease, as well as patients who are ill or have been diagnosed as suffering from a disease or medical condition. The term does not necessarily imply that a subject is treated until total recovery. These terms also refer to the maintenance and/or promotion of health in a subject not suffering from a disease but who may be susceptible to the development of an unhealthy condition. These terms are also intended to include the potentiation or otherwise enhancement of one or more primary prophylactic or therapeutic measure. The terms "treatment," "treat," "attenuate" and "alleviate" are further intended to include the dietary management of a disease or condition or the dietary management for prophylaxis or prevention a disease or condition. A treatment can be patient- or doctor-related.

The term "subject" means any animal, including humans, that could suffer from cognitive aging and thus benefit from one or more of the methods disclosed herein. Generally, the subject is a human or an avian, bovine, canine, equine, feline, hircine, lupine, murine, ovine or porcine animal. A "companion animal" is any domesticated animal, and includes, without limitation, cats, dogs, rabbits, guinea pigs, ferrets, hamsters, mice, gerbils, horses, cows, goats, sheep, donkeys, pigs, and the like. Preferably, the subject is a human or a companion animal such as a dog or cat. The term "elderly" in the context of a human means an age from birth of at least 60 years, preferably above 63 years, more preferably above 65 years, and most preferably above 70 years. The term "older adult" in the context of a human means an age from birth of at least 45 years, preferably above 50 years, more preferably above 55 years, and includes elderly subjects. For other animals, an "older adult" has exceeded 50% of the average lifespan for its particular species and/or breed within a species. An animal is considered "elderly" if it has surpassed 66% of the average expected lifespan, preferably if it has surpassed the 75% of the average expected lifespan, more preferably if it has surpassed 80% of the average expected lifespan. An elderly cat or dog has an age from birth of at least about 7 years.

As used herein, an "effective amount" is an amount that prevents a deficiency, treats a disease or medical condition in a subject or, more generally, reduces symptoms, manages progression of the diseases or provides a nutritional, physiological, or medical benefit to the subject. The relative terms "improved," "increased," "enhanced" and the like refer to the effects of the composition disclosed herein relative to a composition lacking one or more ingredients and/or having a different amount of one or more ingredients, but otherwise identical.

As used herein "lowering" the von Willebrand factor levels in a subject is taken to mean that the von Willebrand factor levels are lower due to use of the compound or composition of the invention. In other words, the von Willebrand factor levels are lower in a treated subject compared to the levels that would have been seen in the same subject if untreated.

The term "blood disorder" includes disorders, disease, or conditions due to abnormalities related to red blood cells, white blood cells, or platelets, or a combination thereof.

Compound or composition thereof

It is understood that according to certain embodiments, the compound of the invention or composition thereof may be a nutraceutical composition, pharmaceutical composition, functional food, functional nutrition product, medical food, medical nutrition product, or dietary supplement.

The terms "nutraceutical" combines the words "nutrition" and "pharmaceutical". It is a food or food product that provides health and medical benefits, including the prevention and treatment of disease. A nutraceutical is a product isolated or purified from foods that is generally sold in medicinal forms not usually associated with food. A nutraceutical is demonstrated to have a physiological benefit or provide protection against chronic disease. Such products may range from isolated nutrients, dietary supplements and specific diets to genetically engineered foods, herbal products, and processed foods such as cereals, soups, and beverages.

The term "nutraceutical" as used herein denotes usefulness in both nutritional and pharmaceutical fields of application. Thus, novel nutraceutical compositions can be used as supplements to food and beverages and as pharmaceutical formulations for enteral or parenteral application which may be solid formulations, such as capsules or tablets, or liquid formulations, such as solutions or suspensions.

The nutraceutical compositions according to the present invention may further contain protective hydrocolloids (such as gums, proteins, modified starches), binders, film-forming agents, encapsulating agents/materials, wall/shell materials, matrix compounds, coatings, emulsifiers, surface active agents, solubilising agents (oils, fats, waxes, lecithins etc.), adsorbents, carriers, fillers, co-compounds, dispersing agents, wetting agents, processing aids (solvents), flowing agents, taste-masking agents, weighting agents, jellyfying agents, gel-forming agents, antioxidants and antimicrobials.

Moreover, a multi-vitamin and mineral supplement may be added to nutraceutical compositions of the invention to obtain an adequate amount of an essential nutrient, which is missing in some diets. The multi-vitamin and mineral supplement may also be useful for disease prevention and protection against nutritional losses and deficiencies due to lifestyle patterns.

The nutraceutical compositions of the invention may be in any galenic form that is suitable for administering to the body, especially in any form that is conventional for oral administration, e.g. in solid forms such as (additives/supplements for) food or feed, food or feed premix, fortified food or feed, tablets, pills, granules, dragees, capsules and effervescent formulations, such as powders and tablets, or in liquid forms, such as solutions, emulsions or suspensions as e.g. beverages, pastes and oily suspensions. The pastes may be incorporated in hard or soft shell capsules, whereby the capsules feature e.g. a matrix of (fish, swine, poultry, cow) gelatine, plant proteins or lignin sulfonate. Examples for other application forms are those for transdermal, parenteral or injectable administration. The dietary and pharmaceutical compositions may be in the form of controlled (delayed) release formulations.

Beverages encompass non-alcoholic and alcoholic drinks as well as liquid preparations to be added to drinking water and liquid food. Non-alcoholic drinks are e.g. soft drinks, sports drinks, fruit juices, teas and milk-based drinks. Liquid foods are e.g. soups and dairy products. The nutraceutical composition comprising the compound of the invention may be added to a soft drink, an energy bar, or a candy.

If the nutraceutical composition is a pharmaceutical formulation the composition further contains pharmaceutically acceptable excipients, diluents or adjuvants then standard techniques may be used for their formulation, as e.g. disclosed in Remington's Pharmaceutical Sciences, 20th edition Williams & Wilkins, PA, USA. For oral administration, tablets and capsules are preferably used which contain a suitable binding agent, e.g. gelatine or polyvinyl pyrrolidone, a suitable filler, e.g. lactose or starch, a suitable lubricant, e.g. magnesium stearate, and optionally further additives.

"Functional food", "functional nutrition product", "medical food" and "medical nutrition product" relate to any healthy food claimed to have a health-promoting or disease-preventing property beyond the basic function of supplying nutrients. The general category of functional foods includes processed food or foods fortified with health-promoting additives, like "vitamin-enriched" products.

A dietary supplement, also known as food supplement or nutritional supplement, is a preparation intended to supplement the diet and provide nutrients, such as vitamins, minerals, fiber, fatty acids, or amino acids, that may be missing or may not be consumed in sufficient quantities in a person's diet. Some countries define dietary supplements as foods, while in others they are defined as drugs or natural health products. Supplements containing vitamins or dietary minerals are included as a category of food in the Codex Alimentarius, a collection of internationally recognized standards, codes of practice, guidelines and other recommendations relating to foods, food production and food safety. These texts are drawn up by the Codex Alimentarius Commission, an organization that is sponsored by the Food and Agriculture Organization of the United Nations (FAO) and the World Health Organization (WHO).

Administration of Compound or Composition Thereof

The compound of the invention or composition thereof may be administered by oral administration, intravenous administration, topical administration, parenteral administration, intraperitoneal administration, intramuscular administration, intrathecal administration, intralesional administration, intracranial administration, intranasal administration, intraocular administration, intracardiac administration, intravitreal administration, intraosseous administration, intracerebral administration, intraarterial administration, intraarticular administration, intradermal administration, transdermal administration, transmucosal administration, sublingual administration, enteral administration, sublabial administration, insufflation administration, suppository administration, inhaled administration, or subcutaneous administration.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

EXAMPLE 1

The following non-limiting example is an experimental example supporting the use of triterpene quinone methides to reduce vWF production in cultured endothelial cells (ECs), a model of human vasculature.

Endothelial Cells and Molecular Reagents

Human induced-pluripotent stem cell derived endothelial cells and accompanying growth media were purchased from Cellular Dynamics International. ECs were cultured according to the manufacturer's protocol (Cellular Dynamics International). ECs were plated at a density of 10'000-15'000 cells/cm$^2$ in culture vessels which have been coated with fibronectin (Invitrogen) and maintained in a low oxygen incubator (37° C., 5% $CO_2$, 5% $O_2$). The EC maintenance media was exchanged every other day and comprised of VascuLife Basal medium +VascuLife VEGF medium complete kit (Lifeline Cell Technologies). For all experiments ECs of passage 0 or 1 were used. The Celastrol used was a synthetic organic chemical manufactured in the United States and purchased from Novus (catalog reference number NBP2-29362). vWF primary antibody was obtained from Abcam (ab6994), tubulin primary antibody was obtained from Abcam (ab7291), and the secondary antibodies were Alexa fluor (anti-mouse and anti-rabbit) obtained from Thermo Fisher Scientific.

Cultured Human Endothelial Cell vWF Expression Assay

Endothelial cells were plated into 96-well glass-bottom plates at a density of 10,000 cells per well. The cells were grown for 4 days in a humidified cell culture incubator at 37° C. until confluency before treatment. Celastrol treatments were freshly prepared from 10 mM frozen stock (in DMSO, stored at −20° C.) by serial diluation in growth medium to the required concentrations: 0.01 µM, 0.1 µM, 1 µM, and 10 µM. The appropriate amount of DMSO was added to the control conditions. On the day of treatment, all media were aspirated from the cells, and 100 µL of celastrol treatment (or control) was added gently to each well, to avoid disruption of the cell monolayer (N=24 per experiment). Treated cells were returned to the cell culture incubator. After 24h, the cells were removed from the incubator and washed once with phosphate-buffered saline (PBS) before being fixed with 4% paraformaldyhde at 37° C. for 5 min. Fixed cells were washed three times with PBS, permeabilized with 0.1% (vol/vol) Triton X-100 in PBS, washed again with PBS, and non-specific antibody binding blocked by 1h incubation with 5% bovine serum albumin (BSA). Cells were then incubated overnight at 4° C. in a primary antibody solution containing 1% BSA and antibodies directed against vWF and tubulin. The cells were washed three times with PBS and incubated for one hour at room temperature in a secondary antibody solution containing fluorescently-tagged antibodies directed against the primary antibodies. Again the cells were washed three times with PBS. They were then incubated in a solution containing 4',6-diamidino-2-phenylindole (DAPI; 1:50,000 dilution; Sigma Aldrich), a fluorescent stain that binds to DNA and allows for visualization of cell nuclei. Image acquisition was achieved using the ImageXpress (Molecular Devices) platform. Quantification of the fluorescence intensity (which is indicative of protein levels) was performed using the MetaXpress software.

Data Analyses

Data are presented as mean±SEM. Statistical significance was computed using one-way ANOVA followed by Tukey's multiple-comparison testing. P less than 0.05 was considered significant.

The figure (FIG. 1) depicts the quantification of the data for human endothelial cells treated with celastrol as described above. On the x axis is the micromolar concentration of celastrol used to treat the cells, and on they axis is the level of vWF expression. The amount of vWF protein expression is normalized by the expression of tubulin, a ubiquitous protein that is not affected by celastrol treatment. Celastrol treatment significantly (***p<0.001) reduces vWF protein expression at concentrations of 1 µMand 10 µM.

REFERENCES

Bockenstedt, P., Greenberg, J. M. & Handin, R. I. (1986) Structural basis of von Willebrand factor binding to platelet glycoprotein Ib and collagen. Effects of disulfide reduction and limited proteolysis of polymeric von Willebrand factor. *J Clin Invest*, 77, 743-749.

Chung, D. W. & Fujikawa, K. (2002) Processing of von Willebrand factor by ADAMTS-13. *Biochemistry*, 41, 11065-11070.

De Meyer, S. F., Stoll, G., Wagner, D. D. & Kleinschnitz, C. (2012) von Willebrand factor: an emerging target in stroke therapy. *Stroke*, 43, 599-606.

Franchini, M. & Lippi, G. (2007) The role of von Willebrand factor in hemorrhagic and thrombotic disorders. *Crit Rev Clin Lab Sci*, 44, 115-149.

Giblin, J. P., Hewlett, L. J. & Hannah, M. J. (2008) Basal secretion of von Willebrand factor from human endothelial cells. *Blood*, 112, 957-964.

Gragnano, F., Sperlongano, S., Golia, E., Natale, F., Bianchi, R., Crisci, M., Fimiani, F., Pariggiano, I., Diana, V., Carbone, A., Cesaro, A., Concilio, C., Limongelli, G., Russo, M. & Calabro, P. (2017) The Role of von Willebrand Factor in Vascular Inflammation: From Pathogenesis to Targeted Therapy. *Mediators Inflamm*, 2017, 5620314.

Gurol, G., Ciftci, I. H., Harman, H., Karakece, E., Kamanli, A. & Tekeoglu, I. (2015) Roles of claudin-5 and von Willebrand factor in patients with rheumatoid arthritis. *Int J Clin Exp Pathol*, 8, 1979-1984.

Horvath, B., Hegedus, D., Szapary, L., Marton, Z., Alexy, T., Koltai, K., Czopf, L., Wittmann, I., Juricskay, I., Toth, K. & Kesmarky, G. (2004) Measurement of von Willebrand factor as the marker of endothelial dysfunction in vascular diseases. *Exp Clin Cardiol*, 9, 31-34.

Jaffe, E. A., Hoyer, L. W. & Nachman, R. L. (1973) Synthesis of antihemophilic factor antigen by cultured human endothelial cells. *J Clin Invest*, 52, 2757-2764.

Jager, A., van Hinsbergh, V. W., Kostense, P. J., Emeis, J. J., Yudkin, J. S., Nijpels, G., Dekker, J. M., Heine, R. J., Bouter, L. M. & Stehouwer, C. D. (1999) von Willebrand factor, C-reactive protein, and 5-year mortality in diabetic and nondiabetic subjects: the Hoorn Study. *Arterioscler Thromb Vasc Biol*, 19, 3071-3078.

Koster, T., Blann, A. D., Briet, E., Vandenbroucke, J. P. & Rosendaal, F. R. (1995) Role of clotting factor VIII in effect of von Willebrand factor on occurrence of deep-vein thrombosis. *Lancet*, 345, 152-155.

Kremer Hovinga, J. A., Coppo, P., Lammle, B., Moake, J. L., Miyata, T. & Vanhoorelbeke, K. (2017) Thrombotic thrombocytopenic purpura. *Nat Rev Dis Primers*, 3, 17020.

Lollar, P. (1991) The association of factor VIII with von Willebrand factor. *Mayo Clin Proc,* 66, 524-534.

Meyer, D., Pietu, G., Fressinaud, E. & Girma, J. P. (1991) von Willebrand factor: structure and function. *Mayo Clin Proc,* 66, 516-523.

Michiels, C. (2003) Endothelial cell functions. *J Cell Physiol,* 196, 430-443.

Rusu, L., Andreeva, A., Visintine, D. J., Kim, K., Vogel, S. M., Stojanovic-Terpo, A., Chernaya, O., Liu, G., Bakhshi, F. R., Haberichter, S. L., Iwanari, H., Kusano-Arai, O., Suzuki, N., Hamakubo, T., Kozasa, T., Cho, J., Du, X. & Minshall, R. D. (2014) G protein-dependent basal and evoked endothelial cell vWF secretion. *Blood,* 123, 442-450.

Seaman, C. D., Yabes, J., Comer, D. M. & Ragni, M. V. (2015) Does deficiency of von Willebrand factor protect against cardiovascular disease? Analysis of a national discharge register. *J Thromb Haemost,* 13, 1999-2003.

Spiel, A. O., Gilbert, J. C. & Jilma, B. (2008) von Willebrand factor in cardiovascular disease: focus on acute coronary syndromes. *Circulation,* 117, 1449-1459.

Vischer, U. M., Barth, H. & Wollheim, C. B. (2000) Regulated von Willebrand factor secretion is associated with agonist-specific patterns of cytoskeletal remodeling in cultured endothelial cells. *Arterioscler Thromb Vasc Biol,* 20, 883-891.

Whincup, P. H., Danesh, J., Walker, M., Lennon, L., Thomson, A., Appleby, P., Rumley, A. & Lowe, G. D. (2002) von Willebrand factor and coronary heart disease: prospective study and meta-analysis. *Eur Heart J,* 23, 1764-1770.

Yau, J. W., Teoh, H. & Verma, S. (2015) Endothelial cell control of thrombosis. *BMC Cardiovasc Disord,* 15, 130.

The invention claimed is:

1. A method for reducing a risk and/or severity of or treatment of a blood disorder in a patient in need thereof, the method comprising administering to the patient a triterpene compound selected from the group consisting of celastrol, pristimerin, and tingenone, and the blood disorder is selected from the group consisting of von Willebrand Factor disease, thrombosis, hemostasis, hypercoagulation, abnormal blood flow, endothelial cell dysfunction, and combinations thereof.

2. The method according to claim 1, wherein the triterpene compound is administered to the patient in an effective amount to lower von Willebrand factor levels in the patient, and the patient is a human subject.

3. The method according to claim 1, wherein the triterpene compound is celastrol.

4. The method according to claim 1, wherein the blood disorder is selected from the group consisting of peripheral thrombosis, cardiac thrombosis, and cerebral thrombosis.

5. The method according to claim 1, wherein the blood disorder is von Willebrand Factor disease, and the patient has another condiction selected from the group consisting of an ApoE4 allele, a cardiovascular disorder, Type I diabetes, Type 2 diabetes, Systemic lupus erythematosus, Active ulcerative colitis, Rheumatoid arthritis, physiological and acute stress, and combinations thereof.

\* \* \* \* \*